(12) United States Patent
Pelissier et al.

(10) Patent No.: US 11,026,774 B2
(45) Date of Patent: Jun. 8, 2021

(54) HERNIA REPAIR PROSTHESES

(71) Applicant: TEXTILE HI-TEC, Verreries-de-Moussans (FR)

(72) Inventors: Edouard Pelissier, Geneuille (FR); Claude Largenton, Saint Lo (FR); Philippe Ngo, Paris (FR)

(73) Assignee: THT BIO-SCIENCE, SOCIETE PAR ACTIONS SIMPLIFIEE, Verreries-de-Moussans ( * ) Notice: Subject to any disclaimer, the term of this patent is extended or adjusted under 35 U.S.C. 154(b) by 313 days.

(21) Appl. No.: 15/738,725

(22) PCT Filed: May 10, 2016

(86) PCT No.: PCT/FR2016/051093
§ 371 (c)(1),
(2) Date: Dec. 21, 2017

(87) PCT Pub. No.: WO2017/013320
PCT Pub. Date: Jan. 26, 2017

(65) Prior Publication Data
US 2018/0185129 A1 Jul. 5, 2018

(30) Foreign Application Priority Data
Jul. 20, 2015 (FR) ...................................... 1556867

(51) Int. Cl.
*A61F 2/00* (2006.01)
(52) U.S. Cl.
CPC .... *A61F 2/0063* (2013.01); *A61F 2002/0072* (2013.01); *A61F 2230/0008* (2013.01);
(Continued)

(58) Field of Classification Search
CPC ............ A61F 2/0063; A61F 2002/0068; A61F 2230/0019; A61F 2250/0051
See application file for complete search history.

(56) References Cited

U.S. PATENT DOCUMENTS

| 2011/0190795 A1* | 8/2011 | Hotter ................... A61F 2/0063 606/151 |
| 2012/0165957 A1* | 6/2012 | Everland ............... A61F 2/0045 623/23.72 |

(Continued)

FOREIGN PATENT DOCUMENTS

| FR | 2 924 330 A1 | 6/2009 |
| WO | 2014/167131 A1 | 10/2014 |
| WO | 2015/011417 A1 | 1/2015 |

OTHER PUBLICATIONS

International Search Report of PCT/FR2016/051093 dated Jul. 29, 2016.

*Primary Examiner* — Sarah A Simpson
(74) *Attorney, Agent, or Firm* — Sughrue Mion, PLLC

(57) ABSTRACT

Prosthesis (1a) for repair of an inguinal hernia, intended to be implanted laparoscopically, comprising openwork fabric of biocompatible material, comprising a first surface, called parietal surface, intended to be placed facing biological tissues of the inguinal region, and a second surface, opposite the first surface, called peritoneal surface, intended to be placed facing the peritoneum, the peritoneal surface comprising, on a portion of the surface thereof, a first zone (6), provided with a non-stick coating, the parietal surface comprising, on a portion of the surface thereof, a second zone (7) provided with a non-stick coating.

12 Claims, 2 Drawing Sheets

(52) U.S. Cl.
CPC ............. *A61F 2230/0019* (2013.01); *A61F 2250/0051* (2013.01)

(56) References Cited

U.S. PATENT DOCUMENTS

| | | | |
|---|---|---|---|
| 2013/0218178 A1* | 8/2013 | Shandas | A61F 2/0063 606/151 |
| 2014/0350580 A1 | 11/2014 | Bell | |
| 2016/0030148 A1 | 2/2016 | Cossa | |
| 2016/0166368 A1 | 6/2016 | Solecki et al. | |
| 2016/0310252 A1* | 10/2016 | Towfigh | A61F 2/0063 |

\* cited by examiner

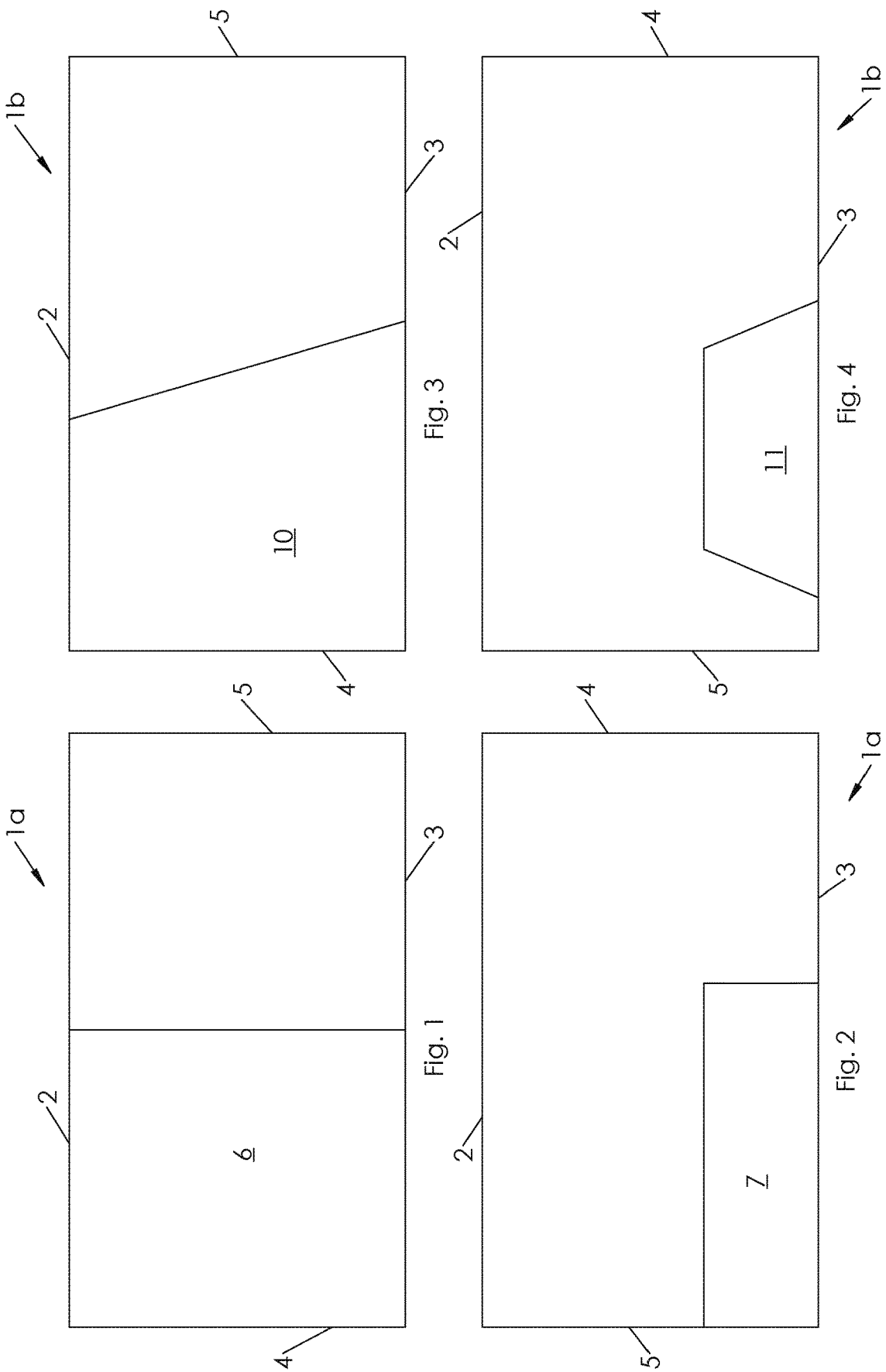

HERNIA REPAIR PROSTHESES

CROSS REFERENCE TO RELATED APPLICATIONS

This application is a National Stage of International Application No. PCT/FR2016/051093 filed May 10, 2016, claiming priority based on French Patent Application No. 1556867 filed Jul. 20, 2015, the contents of all of which are incorporated herein by reference in their entirety.

The present invention concerns prostheses for the repair of hernias, and more particularly prostheses adapted for repair of inguinal hernias.

Hernias are defined as the spontaneous issue, temporary or permanent, of a peritoneal sac containing part or all of one or more viscera or of the greater omentum outside of the limits of the cavity normally containing them, through an area of predictable anatomical weakness, sometimes enabled by a congenital or acquired predisposition.

Hernias can cause pain, difficulty in walking, transit disorders, and they harm the body image.

The most serious complication of hernias is hernia strangulation, which requires emergency surgery. Strangulation of the small intestine, the most frequent and most serious, is responsible for an acute occlusion; its development without treatment results in necrosis of the intestine in the hernial sac and can be life-threatening.

Document WO 2015/011417 describes an intraperitoneal prosthesis, comprising an adhesive face at the peritoneum and a non-adhesive face in the abdominal cavity, in contact with the intestine, for the treatment of ventral hernias, and it seeks to avoid adhesion at the peripheral edge of the prosthesis.

Document FR 2924330 describes an implant specifically designed for prevention or treatment of hernia in proximity to an abdominal wall stoma (ileostomy, colostomy).

Groin hernia is a frequent complaint. Surgical treatment of groin hernia is the most common abdominal surgery.

160,000 cases per year in France (Oberlin et al., *Le traitement des hernies de l'aine en 1998: un exemple de la disparité des pratiques* [*Treatment of groin hernias in 1998: an example of disparity and practices*], Drees, Etudes et Résultats No. 92, 2000), the overall incidence being 272 surgeries per year per 100,000 inhabitants;

800,000 cases in the United States (Aquina et al., *The pitfalls of inguinal herniorrhaphy, surgeon volume matters*, Surgery, 2015);

80,000 cases in Great Britain (Bhattacharjee, *Surgical options in inguinal hernia: which is the best*, Indian J Surg, 68, pp. 191-197, 2006).

Surgical treatment of groin hernias involves men for the most part, with more than eight out of ten surgeries being for men.

Depending on the orifice through which the hernia protrudes, inguinal hernias are distinguished from femoral hernias. Femoral or crural hernias only represent about 3% of groin hernias.

Various classifications of hernias have been proposed (Miserez et al., *The European hernia society groin hernia classification*, Hernia, 2007) and inguinal hernias are divided into three main types, depending on the site of the dehiscence: direct hernias, indirect hernias and mixed hernias. Inguinal hernias are defined by the passage through the *transversalis* fascia, which constitutes the posterior wall of the inguinal canal, of a peritoneal diverticulum, the hernial sac, which may or may not contain viscera. This sac is preceded by a pre-hernial lipoma, varying in size, usually situated above the spermatic cord.

In children, the hernial orifice is always closed by suturing the tissues.

In adults, the raphia methods, by suture (Bassini technique developed in 1887, the Shouldice technique developed in the early 1950s) prevailed until the 1990s, with a high rate of recidivism on the order of 8%, and have been progressively replaced by methods involving the implementation of a prosthesis (Pélissier, *Etat actuel du traitement de la herine inguinale* [*current status of treatment of inguinal hernia*], e-paper from the Academy of surgery 8 (2), pp. 31-33, 2009).

There are currently a wide variety of implants for treatment of abdominal hernias (Zogbi, *The use of biomaterials to treat abdominal hernias*, in Biomaterials applications for nanomedecine, ISBN 978-953-307-661-4, 2011) and more particularly groin hernias (Bilsel et al., *The search for ideal hernia repair, mesh materials and types*, International Journal of Surgery 10, pp. 317-321, 2012). Conventionally, prostheses are pieces of synthetic mesh, most often of polypropylene or polyethylene threads. These meshes cause a fibro-sclerotic reaction of the body, responsible for their incorporation in the tissues, which ensures the soundness of the repair. However, the adhesions can cause side effects when they are done with organs.

Prosthetic repairs of groin hernias have reduced the percentage of recidivism, which is now on the order of 1 to 2%, so that currently the main concern of surgeons is no longer recidivism, but the risk of chronic pain and its impact on quality of life (Shouldice, *International Journal of Clinical Medicine*, 5, pp. 737-740, 2014). The incidence of chronic pain is estimated on average at 10-12%, and it affects activity, including professional activity, in 0.5 to 6% of cases.

There are two broad types of operational techniques for implanting the prosthesis: the Lichtenstein type techniques and the pre-peritoneal techniques.

In the Lichtenstein type techniques, the hernia is approached by direct incision (laparotomy) at the groin, and the prosthesis is attached to the surface of the muscle mass. These techniques have a low percentage of recidivism (on the order of 1 to 2%), but leave exposure to post-operative pain, and particularly chronic pain, as well as cutaneous sensitivity disorders. These complications are related to a risk of damage to sensitive nerves in the inguinal region. This risk is related to the extended dissection, to the risk of catching the nerves in the suture needed to attach the prosthesis, and to the risk of incorporating the nerves in the fibrosclerosis caused by the prosthesis.

In pre-peritoneal techniques, the implant of the prosthesis on the deep face of the muscle mass, in the space between the muscle wall and peritoneum (pre-peritoneal space) can be done:

by endoscopy (laparoscopy, celio-surgery), by
extraperitoneally, called "Total Extraperitoneal Hernioplasty" (TEP),
or intraperitoneally, called "Transabdominal Preperitoneal hernioplasty" (TAPP) (*Guidelines for TAPP and TEP treatment of inguinal hernia, IEHS*, Surg Endosc 25, pp. 2773-2843, 2011), or by direct Kugel incision, TIPP (Transinguinal Preperitoneal Patch), TREPP (Trans Rectus sheath Extra-Peritoneal Procedure) and ONSTEP (Anderson et al., *The Initial Experience of Introducing the Onstep Technique for Inguinal Hernia Repair in a General Surgical Department*, Scandinavian Journal of Surgery, 2014).

The pre-peritoneal techniques by endoscopy or open surgery have the particular advantage, compared to the Lichtenstein type techniques, of reducing the time off work after which most patients are able to return to work. For example, according to French practice, for a job requiring light physical work, the time off work according to health insurance is 10 days for treatment by celioscopy, and 21 days for treatment by open surgical repair.

The pre-peritoneal techniques by laparoscopy or open surgery also have the advantage of reducing hospitalization times.

These techniques are as effective as the Lichtenstein technique, with a comparable percentage of recidivism, and result in less pain and fewer sensitivity disorders (Bobo et al., *Meta-analysis of randomized controlled trials comparing Lichtenstein and totally extraperitoneal laparoscopic hernioplasty in treatment of inguinal hernias, Journal of surgical research* 192, pp. 409-420, 2014). This is due to the absence of extended dissection of the inguinal canal, to the absence of contact of the prosthesis with the nerves of the inguinal canal and to the fact that the prosthesis requires little or no attachment, being applied against the wall by abdominal pressure. Multiple studies have shown that, compared to the direct approach methods, the pre-peritoneal prostatic repair offers:

less postoperative pain, and allows a faster resumption of activity;
less chronic pain, fewer sensitivity disorders;
better quality of life.

The pre-peritoneal prosthesis leads to adherence of the prosthesis to the bladder and the peritoneum, which causes dissection difficulties during a subsequent radical prostatectomy. These risks have been mentioned in the literature for more than 15 years, with no satisfactory solution being proposed:

Picozzi et al., *Worl J Urol* 33, pp. 69-67, 2015;
Spernat et al., *Prostate Int* 2(1), pp. 8-11, 2014;
Haifler et al., *Journal of Endourology,* 26(11), pp. 1458-1462, 2012;
Peeters et al., *British Journal of Surgery* pp, pp. 431-435, 2012;
Neff et al., *Urologic Oncology* 29, pp. 66-69, 2011;
Do et al., *Urology* 77(4), pp. 963-967, 2011;
Saint Elie et al., *Urology* 76(5), pp. 1078-1082, 2010;
Hocaoglu et al., *Bju Int* 106, pp. 1628-1631, 2010;
Siddiqui et al., *Urology* 75(5), pp. 1079-1082, 2010;
Lallas et al., *JSLS* 13, pp. 142-147, 2009;
Tsivian et al., *Hernia* 13, pp. 523-527, 2009;
Thomas et al., *J Am Coll Surg*, pp. 371-376, 2009;
Vijan et al., *Hernia* 12, pp. 415-419, 2008;
Stolzenburg et al., *World J Urol* 23, pp. 295-299, 2005;
Stolzenburg et al., *Adult Urology*, pp. 325-331, 2005;
Joseph et al., *JSLS* 9, pp. 368-369, 2005;
Amid, *Hernia* 8, pp. 169-170, 2004;
Brown et al., *Urology* 63(2), pp. 380vii-ix, 2004;
Cooperberg et al., *Surgery*, pp. 452-453, 2004;
Cook et al., *BJU Int* 91, pp. 729, 2003;
Borchers et al., *Urologia Internationals,* 67 pp. 213-215, 2001;
Stoppa et al., *Hernia* 2, pp. 35-38, 1998.

Urological surgeons face dissection problems in approaching the prostate due to the adherence of the prosthesis to the anterior face of the bladder and to the prostatic region. Moreover, a radical prostatectomy is normally completed by ablation of the lymph nodes draining the prostate, in an area between the iliac vessels and the obturator neurovascular pedicle (lymph node excision). However, this area is also covered by the prosthesis, and the adherence to the vessels runs the risk of vascular injury, the consequences of which can be dramatic. Therefore, lymph node excision is only performed in half of the cases, which can have a negative impact on the prognosis of cancer.

In bladder cancer in men, the prostate can be removed at the same time as the bladder. It has been determined that inguinal hernia treatment prosthesis causes dissection difficulties during a radical cystoprostatectomy, and can prevent or reduce the extent of the lymphadenectomy (Jones, *Urology* 70(6), pp. 1079-1081, 2007).

Reducing the adherence of the prosthesis to the bladder, to the prostate and to the lymph node excision area would be long-awaited progress, facilitating radical prostatectomy and lymph node excision in patients who have previously had hernia treatment by pre-peritoneal prosthesis. This progress is all the more desirable since prostate cancer in France, according to the Institut de veille sanitaire [Institute for healthcare supervision], is more frequent in men, with 57,000 new cases per year (Binder et al., ISBN 978-2-11-138316-6, 2012), prostate cancer being one of the most frequent in men, all countries taken together.

A first object of the invention is to propose prostheses, for the treatment of inguinal hernias, facilitating subsequent surgery, particularly radical prostatectomy or radical cysto-prostatectomy.

A second object of the invention is to propose prostheses for the treatment of inguinal hernias, facilitating subsequent lymphadenectomy during treatment of prostate or bladder cancer.

A third object of the invention is to propose pre-peritoneal prostheses for the treatment of inguinal hernias, reducing the risks of adherence between the prosthesis and the viscera.

To these ends, according to a first aspect a prosthesis is proposed for repair of an inguinal hernia, intended to be implanted preperitoneally by endoscope or open surgery, comprising openwork fabric of biocompatible material, comprising a first surface, called parietal surface, intended to be placed facing biological tissues of the inguinal region, and a second surface, opposite the first surface, called peritoneal surface, intended to be placed facing the peritoneum and the anterior face of the bladder, the peritoneal surface comprising, on a portion of the surface thereof, a first zone provided with a non-stick coating, the parietal surface comprising, on a first portion of the surface thereof, a second zone provided with a non-stick coating.

By this disposition, during inguinal hernia repair, the first zone provided with a non-stick coating (called first non-stick zone) can be placed facing the bladder-prostate system and the second zone provided with a non-stick coating (called second non-stick zone) can be placed facing the lymph node excision area. The breadth of the parietal surface, outside the second non-stick zone, preserves the adhesive ability of the prosthesis.

The term "non-stick coating" here designates the presence of a non-stick material on the surface of the fabric of the prosthesis, and/or a slightly roughened surface condition.

The non-stick coating in the first non-stick zone can be identical or different from the non-stick coating in the second non-stick zone. Thus, for example a silicon- or hydrogel-based coating forms the first non-stick zone, the second non-stick zone being defined by the presence, in said second zone, of a very slight surface roughness.

According to various implementations, the non-stick coating is in the form of a continuous film, or in the form of strips or dots. The term "dots" here designates an area of reduced size; said dots may be in the form of a regular pattern, or randomly disposed.

The first and second non-stick zones are disposed on two opposite faces of the prosthesis. Advantageously, when the prosthesis is viewed from the top, the first non-stick zone and the second non-stick zone are not substantially disposed one above the other. By this disposition, the presence of a non-stick coating does not result in a significant excess thickness in the prosthesis, which could hinder its insertion into a trocar.

According to the present application, the term "fabric" is understood as any arrangement or assembly of threads, fibers, filaments and/or multi-filaments, for example obtained by knitting, weaving, braiding or non-woven, and the term "openwork fabric" is understood as any fabric for which the arrangement of threads comprising it define apertures, alveoli, pores or hollows that can constitute channels opening into both sides of the fabric.

Various additional characteristics can be foreseen, alone or in combination:
- the first non-stick zone extends over a surface on the order of 30% to 70% of the surface area of the peritoneal surface;
- the prosthesis being rectangular in shape, the first non-stick zone extends over the full width of the prosthesis, from one side edge of the prosthesis;
- the prosthesis being rectangular in shape, the second non-stick zone extends over a width of between one-fourth and one-half of the width of the prosthesis;
- the first non-stick zone and/or the second non-stick zone comprise a non-stick coating defining a continuous film;
- the non-stick coating of the first non-stick zone and/or of the second non-stick zone is discontinuous and comprises strips or dots;
- the openwork fabric is produced from polyethylene, polypropylene, polytetrafluoroethylene, polyethylene terephthalate, polyvinylidene fluoride (PVDF);
- the first non-stick zone and/or the second non-stick zone comprise a non-absorbable film;
- the first non-stick zone and/or the second non-stick zone comprise an absorbable gel;
- the fabric comprises a first portion, called upper portion, intended to be placed facing the anterior muscular wall and the pectineal ligament, and a second portion, called the lower portion, intended to be placed laterally facing the pubis and iliac and spermatic vessels, and part of the psoas muscle, the upper portion representing between one half and two-thirds of the surface area of the prosthesis, the fabric comprising a line defining a border between the upper part and the lower part;
- the line defining the border between the upper part and the lower part of the prosthesis comprises a seam;
- the prosthesis is provided with means for indicating the orientation of the prosthesis;
- said means of indicating the orientation of the prosthesis comprises an area having a different color from the rest of the prosthesis;
- the fabric being in the form of a tricot, the area of different color is obtained by knitting a thread of a color different from the thread or threads used for the knitting of the rest of the fabric, or by printing on the fabric.

Other objects and advantages of the invention will be seen from the description of embodiments, provided below with reference to the appended drawings in which:

FIG. 1 is a top view of a prosthesis according to a first embodiment, the visible surface being the peritoneal surface;

FIG. 2 is a top view of the prosthesis of FIG. 1, the visible surface being the parietal surface;

FIG. 3 is a top view of a prosthesis according to a second embodiment, the visible surface being the peritoneal surface;

FIG. 4 is a top view of the prosthesis of FIG. 3, the visible surface being the parietal surface;

Figure 5:
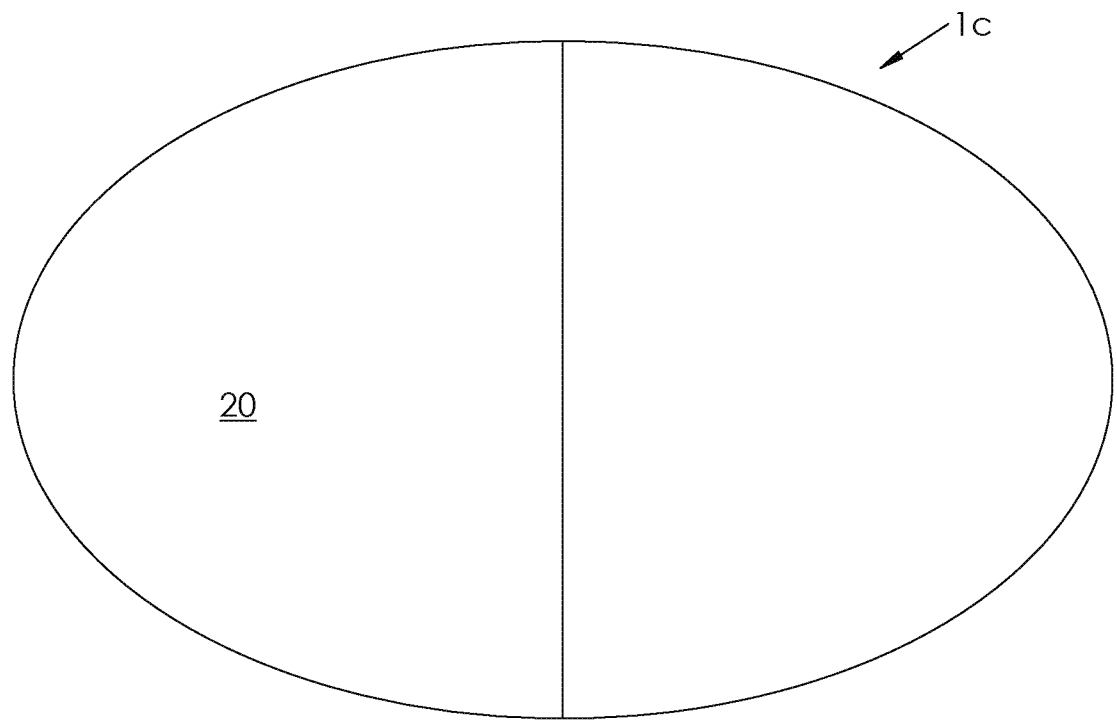
FIG. 5 is a top view of a prosthesis according to a third embodiment, the visible surface being the peritoneal surface.

The prostheses described below, per FIGS. 1 to 6, are in reference to repair of an inguinal hernia, and are intended to be implanted by pre-peritoneal endoscopy or open surgery. However, it is understood that the prostheses can also be used advantageously in other surgical treatments, in which there are problems similar to those identified in the state-of-the-art presented in the introduction.

The prostheses for repair of an inguinal hernia are represented in the figures for a hernia on the right side. It is understood that a similar prosthesis, not shown, can be employed for repairing an inguinal hernia on the left side, the right and left prostheses being symmetrical with each other.

The prostheses that will be described are of the flat implant type. However, it is understood that the invention also relates to so-called anatomical or three-dimensional prostheses, produced by thermoforming, or comprising seams, so as to follow the anatomical shapes of the inguinal space.

The prostheses that will be described comprise a fabric, particularly an openwork fabric of biocompatible material, comprising a first surface, called parietal surface, intended to be placed facing biological tissues of the inguinal region, and a second surface, opposite to the first surface, called the peritoneal surface intended to be placed facing the peritoneum.

The peritoneal surface comprises, on a portion of the surface thereof, a first zone provided with a non-stick coating and the parietal surface comprises, on a portion of the surface thereof, a second zone provided with a non-stick coating.

The two zones of non-stick coating correspond to the bladder-prostate system and the lymph node excision area. The parietal surface of the prosthesis is applied against the muscle wall. The opposite surface, called peritoneal, faces the deep face of the peritoneum and the anterior face of the bladder.

More specifically, the parietal surface of the prosthesis covers the anatomical area of lymph node excision, and the peritoneal surface of the prosthesis is partly in contact with the peritoneum and partly in contact with the bladder-prostate system, in a proportion of one-third/two-thirds, half and half.

The prostheses implemented according to the present invention are advantageously unalterable in a biological environment, non-allergenic, non-carcinogenic, sterilizable, and have a low inflammation reaction.

In some implementations, the prosthesis is a fabric, particularly an openwork fabric, formed from a non-absorbable material such as polyamide, polyester, particularly polyethylene terephthalate, polypropylene, polytetrafluoroethylene, vinylidene polyfluoride.

In other implementations, the prosthesis is a fabric, particularly an openwork fabric formed from an absorbable material such as polyglactin.

Advantageously, when the fabric forming the prosthesis is not very transparent, the underlying anatomical areas are indicated on the prosthesis by marking, for example in the form of lines. Said marking enables areas to be delineated in which an attachment by stapling is possible, if appropriate, and to indicate areas in which attachment by stapling should be avoided.

In one implementation, the non-stick material is in the form of a non-absorbable film, for example polytetrafluoroethylene (PTFE).

In other implementations, the non-stick material is of a collagen, silicon or polyurethane base.

In other implementations, the prosthesis comprises a mixture of absorbable and non-absorbable materials. In particular implementations, the prosthesis comprises a fabric, particularly in openwork fabric of polypropylene or a polypropylene-polyethylene terephthalate mixture, the first and second non-stick zones being formed of a hydrogel-based coating, said coating being in the form of a continuous film, or in the form of strips or dots.

Advantageously, the non-stick material has a slight wettability (or hydrophilic property), and is for example based on polytetrafluoroethylene, or its stretched form after heating called expanded polytetrafluoroethylene. In other embodiments, the non-stick material is based on polydimethylsiloxane or polyvinyl fluoride.

Advantageously, the non-stick material is coated on the fabric, particularly the openwork fabric, of the prosthesis. For example, the prosthesis comprises a local coating of a collagen-based material.

In particular implementations, the prosthesis is formed from a fabric, particularly an openwork fabric, of polyester, provided with a first non-stick zone and a second non-stick zone formed by a collagen-based coating, said coating being in the form of a continuous film, or in the form of strips or dots.

In other implementations, the prosthesis is formed from a fabric, particularly an openwork fabric of polypropylene, provided with a first non-stick zone and a second non-stick zone formed by a collagen-based coating, said coating being in the form of a continuous film, or in the form of strips or dots.

In other particular implementations, the prosthesis is based on polytetrafluoroethylene, particularly expanded polytetrafluoroethylene, and comprises a first non-stick zone and a second non-stick zone that are smooth, the rest of the surfaces of the prosthesis being striated.

In other implementations, the non-stick material comprises an absorbable gel, for example based on hyaluronic acid, or a mixture of atelocollagen and maltodextrin.

In another implementation, the non-stick material comprises an absorbable film, for example based on regenerated and oxidized cellulose, or based on a mixture of polylactic acid and caprolactone, or based on a mixture of hyaluronic acid and carboxymethyl cellulose, or based on a mixture of collagen, polyethylene glycol and glycerol.

Examples will now be described of the geometry of the prostheses.

In the embodiment of FIGS. 1 to 4, the prosthesis 1a, 1b is generally rectangular in shape and flat, and comprises an upper longitudinal edge 2, a lower longitudinal edge 3 and two lateral edges 4, 5.

In the embodiment of FIGS. 1 and 2, the first non-stick coating area 6, on the peritoneal surface, extends over a substantially rectangular surface, over the full width of the prosthesis and over a length of between one-third and two-thirds of the length of the prosthesis. Thus, by way of example, when the prosthesis is rectangular, 15 cm long and 10 cm wide, the first non-stick coating area 6 extends over 5 to 8 cm, from the lateral edge 4. This disposition makes it possible to prevent the adherence of the prosthesis 1a to the anterior face of the bladder-prostate system. As a variant of embodiment, not shown, the non-stick zone 6 is offset relative to the lateral edge 4.

In the embodiment of FIGS. 1 and 2, the second non-stick coating area 7, on the parietal surface, extends over a substantially rectangular surface, over one-third to one-half the width of the prosthesis 1a and over substantially half the length of the prosthesis 1a. The second non-stick coating area 7, on the parietal surface, is situated in the inferolateral angle of the prosthesis 1a. Thus, by way of example, when the prosthesis is rectangular, 15 cm long and 10 cm wide, the second non-stick coating area 7 extends over 5 to 8 cm, from the lateral edge 5, and extends over a width of about 3.5 cm. The non-stick zone can be offset relative to the side 5, so as to leave a limited adhesive zone outside the vessels.

In the embodiment of FIGS. 3 and 4, the first zone 10 of non-stick coating, on the peritoneal surface, extends over a substantially trapezoidal surface, the height of which is substantially equal to the width of the prosthesis 1b, the large side being situated in the vicinity of the lower longitudinal edge 3 of the prosthesis 1b, the small side being situated in the vicinity of the upper longitudinal edge 2 of the prosthesis 1b. Thus, by way of example, when the prosthesis 1b is rectangular, 15 cm long and 10 cm wide, the large side of the zone 10 of non-stick coating measures between 5 and 8 cm, the small side measuring between 3 and 7 cm.

In the embodiment of FIGS. 3 and 4, the second zone 11 of non-stick coating, on the parietal surface, extends over a substantially trapezoidal surface area, the large side of which extends substantially over the lower longitudinal edge 3 of the prosthesis 1b. By way of example, the prosthesis has a length of 15 cm and a width of 10 cm, the second zone 11, trapezoidal in shape, extends over a height of 3 to 5 cm, its large side measuring 5 to 6 cm, and its small side measuring from 1 to 2 cm less than its large side. Advantageously, this disposition makes it possible to maintain an adhesive zone of the prosthesis to the parietal plane of about 2 cm between the lateral edge 4 of the prosthesis 1b and the second zone 11. As a variant, the trapezoidal non-stick zone is offset relative to the edge 5, so as to leave an adhesive zone a little more extended.

Figure 6:
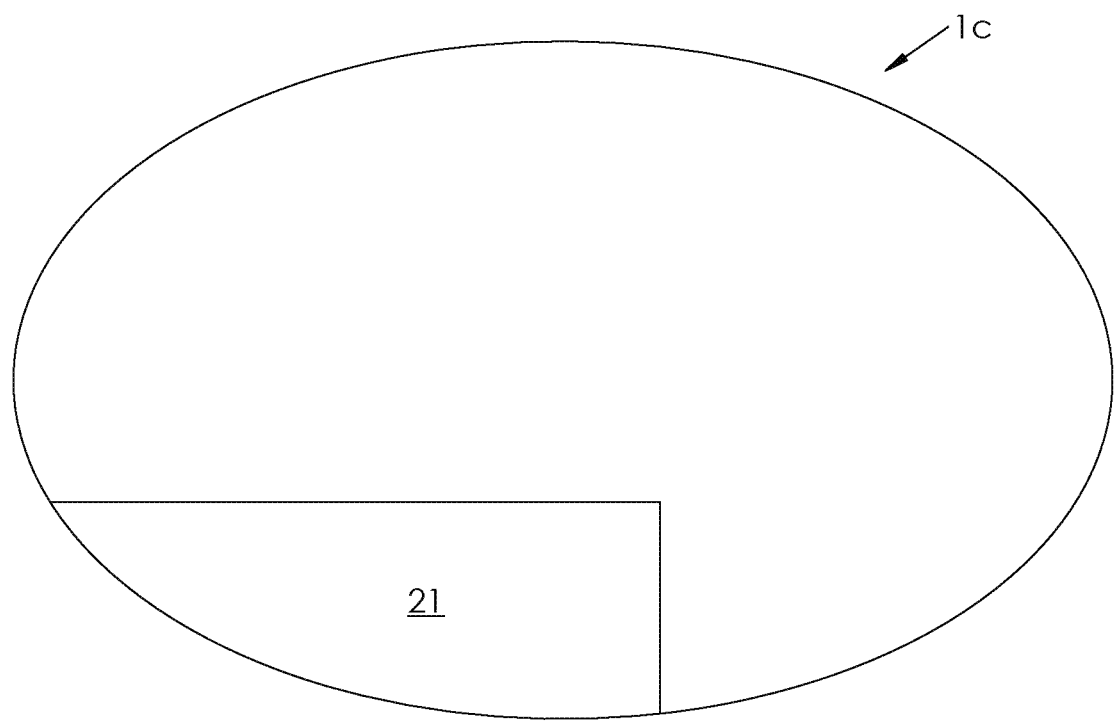
FIG. 6 is a top view of the prosthesis of FIG. 5, the visible surface being the parietal surface.

In the embodiment of FIGS. 5 and 6, the prosthesis 1c is oval-shaped. The first zone 20 of non-stick coating on the peritoneal surface extends over the full width of the prosthesis 1c and over one-half and up to two-thirds of the surface area of the prosthesis 1c. The second zone 21 of non-stick coating, on the parietal surface, extends over substantially one-half of the length of the prosthesis 1c.

Advantageously, the prosthesis is of the anatomical type and comprises a first portion, called upper portion, intended to be placed facing the anterior muscle wall and the pectineal ligament, and a second portion, called the lower portion, intended to be placed laterally facing the pubis and iliac and spermatic vessels, and a portion of the psoas muscle, the upper portion representing between one-half and two-thirds of the surface area of the prosthesis. The fabric comprises a line defining a border between the upper portion and the lower portion, said line advantageously comprising a seam. Said seam facilitates, during the unfolding of the prosthesis, its adaptation to the anatomical shapes of the inguinal region. The upper portion of the prosthesis serves for the attachment thereof, by known means (for example glue, staple), said attachment not being mandatory, since as was previously mentioned, the prosthesis is applied against the wall by abdominal pressure Advantageously, the prosthesis is provided with a means of indicating its orientation, for example one zone having a different color from the rest of the prosthesis. Since the fabric is in the form of a tricot, the area of different color is obtained by knitting a thread of a color different from the thread or threads used for the knitting of the rest of the fabric, or by printing.

In other implementations, not shown, the prosthesis is intended for the treatment of urinary incontinence, in the form of a urethral sling.

The implantation of slings is a known treatment of urinary incontinence, such slings being in the form of a mesh made of a polymer material forming a hammock to support the urethra. The same principle is conventionally used for the treatment of incontinence associated with cystocele, a variety of genital prolapse often described by the expression "bladder descent," this prolapse resulting from shifting of the bladder wall which unfolds the anterior wall of the vagina and forms a bulge. This treatment is known by some as TICT (Leanza et al., *How to prevent mesh erosion in transobturator tension-free incontinence cystocele treatment TICT: a comparative survey*, G. Chir, pp. 21-25, 2015). The operation is done vaginally with incision of the anterior wall of the vagina to implant the hammock, and the two ends of the sling are inserted on each side by means of solid trocars.

One of the complications of these prostheses is the ulceration of the vaginal wall or urethra, in contact with the prosthetic material with the externalization of the prosthesis into the vagina, infection, pain, bleeding, sexual problems, and sometimes ulceration of the bladder.

The incidence of complications varies, depending on the different techniques of placement, and the experience of the surgeons (Surkont et al., *Long term risk of complications after mid-urethral slings IVS implantation Ann Agri Environ Med*, 22(1), pp. 163-166, 2015). This incidence is:
  about 5% in the Leanza et al. series (Leanza et al., *How to prevent mesh erosion in transobturator tension-free incontinence cystocele treatment TICT: a comparative survey*, G. Chir, pp. 21-25, 2015);
  4.3 to 13.8% in the Boudry et al. series (*Sling exposure after treatment of urinary incontinence with sub-urethral transobturator slings, Eur J Obstet Gynecol Reprod Biol*, 176, pp. 191-196, 2014);
  15% in the Viereck et al. series (*Midurethral sling incision: indications and outcomes, Int Urogynecol J*, 24, pp. 645-653, 2013);
  11.9% in the Taner et al. series (*Perioperative and postoperative complications after Ophira mini sling operations, Arch Gynecol Obstet*, 291, pp. 341-346, 2015).

In a series of 111 women suffering from complications from the prosthesis, extrusion represents, according to Hansen et al., 65% of the cases (*Long term follow-up of treatment for synthetic mesh complications, Female Pelvic Med Reconstr Surg*, 20, pp. 126-130, 2014).

Bowel cancer cases have been observed after sacrocolpopexy, chronic irritation by the prosthesis being a contributing factor to the appearance of these cancers (Ahuja et al., *Bowel cancer and previous mesh surgery, Gynecol Surg*, 8, pp. 217-221, 2011).

As indicated in the document FR 2802798, devices are known for treating urinary incontinence that are in the form of a strap supporting the urethra, these straps being capable of causing friction in the region of the vagina, urethra or bladder, resulting in erosion, inflammation or infections, and even causing the rejection of the strap and requiring its removal. To attempt to resolve these problems, the document FR 2802798 proposes attaching, on one face of the sling forming the strap, a cushioning pad of foam, or a capsule containing air, water, oil or a silicon gel, the thickness of the pad being 20 times that of the sling.

Implanting a sling furnished with such a pad or capsule is complex. In particular, the presence of the pad or capsule makes insertion by trocar very difficult and even impossible.

Sling removal can require invasive or multiple surgeries (Braun et al., *Mesh removal following transvaginal mesh placement: a case series of* 104 *operations, Int Urogynecol J*, 21, pp. 423-430, 2010), and it is sometimes impossible to completely remove the sling, thus making the complications of the prosthesis permanent, particularly the presence of pain.

The present inventors propose, to reduce the risks associated with slings for treatment of incontinence, locally modifying the prosthesis by providing a first non-stick zone and a second non-stick zone, each placed on one surface of the prosthesis.

The fabric used for the urethral support prosthesis is advantageously suppler than material used for producing a prosthesis for inguinal hernia repair. This arrangement makes it possible to preserve the suppleness and flexibility of the pelvic floor, enabling adaptation to movements and forces associated with daily life, such as coughing, defecation, walking, sexual relations.

The fabric used advantageously has pores of more than 2 mm opening, and low density of less than 35 $g/m^2$.

The urethral support prosthesis advantageously has a non-stick coating on its face in contact with the vaginal wall (called vaginal face) and/or a non-stick coating on its face in contact with the urethra and/or the bladder (called bladder-urethra face).

The term "non-stick coating" here designates the presence of a non-stick material on the surface of the fabric of the prosthesis, and/or a slightly roughened surface condition.

The non-stick coating in the first non-stick zone can be identical or different from the non-stick coating in the second non-stick zone. Thus, for example a silicon- or hydrogel-based coating forms the first non-stick zone, the second non-stick zone being defined by the presence, in said second zone, of a very slight surface roughness.

Depending on various implementations, the coating is in the form of a continuous film, or in the form of strips or dots. The term "dots" here designates an area of reduced size; said dots may be in the form of a regular pattern, or randomly disposed.

In one implementation, the urethral support prosthesis for treatment of incontinence comprises a non-stick zone which extends over the full width of the sling and measures, for example, between 3 and 4 cm long on the vaginal face, and between 1 cm and 2.5 cm on the bladder-urethra face.

In one implementation, the prosthesis for treatment of cystocele comprises a central portion and arms, the central portion comprising a non-stick zone which covers more than 80% of the surface of said central portion, on one of its faces and leaves free a peripheral edge of said central portion, over a width of several millimeters, for example between 5 mm and 15 mm.

In other implementations, the prosthesis is adapted for the treatment of genital prolapse and is intended to be placed in contact with the posterior vaginal wall, the prosthesis comprising, on the face in contact with the vaginal wall, at least one continuous or discontinuous non-stick zone, for example in the form of strips or dots.

The invention claimed is:

1. A prosthesis for repair of an inguinal hernia, configured to be implanted preperitoneally by endoscope or open surgery, comprising openwork fabric of biocompatible material, comprising a first surface, called parietal surface, configured to be placed facing biological tissues of the inguinal region, and a second surface, opposite the first surface, called peritoneal surface, configured to be placed facing the peritoneum and the anterior face of the bladder, wherein the peritoneal surface comprises, on a portion of the surface thereof, a first zone provided with a non-stick coating, the parietal surface comprising, on a portion of the surface thereof, a second zone provided with a non-stick coating, the prosthesis being rectangular in shape, the first zone is extended over the full width of the prosthesis from one lateral edge of the prosthesis, the second zone is extended over a width of between one-third and one-half of the width of the prosthesis; wherein the first zone and the second zone are not substantially disposed one above the other, when the prosthesis is viewed from a top side.

2. The prosthesis according to claim 1, wherein the first zone extends over a surface area on the order of 30% to 70% of the total surface area of the peritoneal surface.

3. The prosthesis according to claim 1, wherein the first zone and/or the second zone comprises a non-stick coating defining a continuous film.

4. The prosthesis according to claim 1, wherein the non-stick coating of the first zone and/or of the second zone is discontinuous and comprises strips or dots.

5. The prosthesis according to claim 1, wherein the openwork fabric is produced from polyethylene, polypropylene, polyethylene terephthalate, polytetrafluoroethylene, vinylidene polyfluoride.

6. The prosthesis according to claim 1, wherein the first zone and/or the second zone comprises a non-absorbable film.

7. The prosthesis according to claim 1, wherein the first zone and/or the second zone comprises an absorbable gel.

8. The prosthesis according to claim 1, wherein the openwork fabric comprises a first portion, called an upper portion, configured to be placed facing the anterior muscular wall and the pectineal ligament, and a second portion, called a lower portion, configured to be placed laterally facing the pubis and iliac and spermatic vessels, and part of the psoas muscle, the upper portion representing between one-half and two-thirds of the surface area of the prosthesis, the openwork fabric comprising a line defining a border between the upper portion and the lower portion.

9. The prosthesis according to claim 8, wherein the line defining the border between the upper portion and the lower portion of the prosthesis comprises a seam.

10. The prosthesis according to claim 1, further provided with means for indicating orientation of the prosthesis.

11. The prosthesis according to claim 10, wherein said means for indicating the orientation of the prosthesis comprises an area having a different color from the rest of the prosthesis.

12. The prosthesis according to claim 11, wherein the openwork fabric being in the form of a tricot, the area of different color is obtained by knitting a thread of a color different from thread or threads used for knitting the rest of the openwork fabric, or by printing on the openwork fabric.

* * * * *